United States Patent
Parks, II et al.

(10) Patent No.: US 7,839,492 B2
(45) Date of Patent: Nov. 23, 2010

(54) LASER-INDUCED FLUORESCENCE FIBER OPTIC PROBE MEASUREMENT OF OIL DILUTION BY FUEL

(75) Inventors: James E. Parks, II, Knoxville, TN (US); William P. Partridge, Jr., Oak Ridge, TN (US)

(73) Assignee: UT-Battelle, LLC, Oak Ridge, TN (US)

( * ) Notice: Subject to any disclaimer, the term of this patent is extended or adjusted under 35 U.S.C. 154(b) by 232 days.

(21) Appl. No.: 12/137,964

(22) Filed: Jun. 12, 2008

(65) Prior Publication Data

US 2009/0310127 A1  Dec. 17, 2009

(51) Int. Cl.
*G01N 33/28* (2006.01)
(52) U.S. Cl. ...................................... 356/70
(58) Field of Classification Search ................ None
See application file for complete search history.

(56) References Cited

U.S. PATENT DOCUMENTS 5,742,064 A * 4/1998 Infante ..................... 250/458.1
5,843,783 A   12/1998 Rutledge et al.
7,410,793 B2 * 8/2008 Boege et al. ............. 435/288.7

OTHER PUBLICATIONS

Jim Parks, et al., "Rapid In Situ Measurement of Fuel Dilution of Oil in a Diesel Engine using Laser-Induced Fluorescence Spectroscopy," SAE International, Oct. 1, 2007.

Brian West, et al., Assessing Reductant Chemistry During In-Cylinder Regeneration of Diesel Lean NOx Traps, SAE International, 2004.

Jim Parks, et. al., "In Situ Measurement of Fuel Absorption into the Cylinder Wall Oil Film During Engine Cold Start," SAE Internationa, 1998.

J.E. Parks, II, et al., "In Situ Measurement of Fuel in the Cylinder Wall Oil Film of a Combustion Engine by LIF Spectroscopy," Applied Spectroscopy, 1998, pp. 112-118, vol. 52, No. 1.

* cited by examiner

*Primary Examiner*—Gregory J Toatley
*Assistant Examiner*—Amanda H Merlino
(74) *Attorney, Agent, or Firm*—Klarquist Sparkman, LLP

(57) ABSTRACT

Apparatus for detecting fuel in oil includes an excitation light source in optical communication with an oil sample for exposing the oil sample to excitation light in order to excite the oil sample from a non-excited state to an excited state and a spectrally selective device in optical communication with the oil sample for detecting light emitted from the oil sample as the oil sample returns from the excited state to a non-excited state to produce spectral indicia that can be analyzed to determine the presence of fuel in the oil sample. A method of detecting fuel in oil includes the steps of exposing a oil sample to excitation light in order to excite the oil sample from a non-excited state to an excited state, as the oil sample returns from the excited state to a non-excited state, detecting light emitted from the oil sample to produce spectral indicia; and analyzing the spectral indicia to determine the presence of fuel in the oil sample.

19 Claims, 14 Drawing Sheets

LASER-INDUCED FLUORESCENCE FIBER OPTIC PROBE MEASUREMENT OF OIL DILUTION BY FUEL

STATEMENT REGARDING FEDERALLY SPONSORED RESEARCH

The United States Government has rights in this invention pursuant to contract no. DE-AC05-00OR22725 between the United States Department of Energy and UT-Battelle, LLC.

CROSS-REFERENCE TO RELATED APPLICATIONS

None

NAMES OF PARTIES TO A JOINT RESEARCH AGREEMENT

Cummins Engine Company

BACKGROUND OF THE INVENTION

It has become desirable to measure the amount of fuel that has contaminated or diluted oil, usually motor oil. In one example, diesel engine technology has advanced significantly over the last decade. Modern diesel engines utilize advanced injector technology to enable multiple injections of fuel per combustion cycle. Precise control of injection timing allows optimization of engine efficiency, engine out emissions, and engine noise, vibration, and harshness. Furthermore, engines are being operated under specific modes to enable after treatment devices in the exhaust system to control pollutants.

One application where the control of fuel injection offers a great advantage is the operation of the diesel engine in net-fuel-rich modes to regenerate lean NOx trap catalysts. The regeneration is necessary for catalyst operation which reduces engine out NOx to regulated levels. During engine operation for catalyst regeneration, extra fuel is injected into the cylinder often in conjunction with throttling or higher exhaust gas recirculation rates to generate rich exhaust. The reductants present in the rich exhaust regenerate the catalyst, and specific parameters of the engine rich mode are adjusted to control both the overall magnitude and chemistry of the exhaust reductant mixture. However, extra fuel injection into the cylinder can lead to other issues of concern such as torque control, noise and vibration control, and oil dilution. In some cases oil dilution by diesel fuel can occur at levels that may impact engine durability.

A challenge for diesel automotive engineers is to establish lean NOx trap regeneration strategies that optimally regenerate the lean NOx trap without creating undesirable secondary emissions (e.g., soot or unburned HCs) in the tailpipe and without causing significant fuel dilution of the engine oil. Fuel impingement of the cylinder wall oil film becomes more likely as the extra fuel injection timing is further delayed from top dead center. Injection timing also affects the reductant chemistry produced. Thus, optimization of the lean NOx trap reductant chemistry and minimization of fuel dilution are linked; both are affected by enrichment parameters. Measurement and feedback on the dilution of oil by fuel during the process is valuable in efficiently determining the optimal conditions to operate the engine.

Although an example has been set forth above to show need and utility of the invention, there are various and sundry other circumstances in which it is desirable to measure at least one of the amount, concentration, and addition (or leakage) rate of fuel that has contaminated or diluted oil, usually, but not always, motor oil.

BRIEF SUMMARY OF THE INVENTION

In accordance with one aspect of the present invention, the foregoing and other objects are achieved by apparatus for detecting fuel in oil includes an excitation light source in optical communication with an oil sample for exposing the oil sample to excitation light in order to excite the oil sample from a non-excited state to an excited state and a spectrally selective device in optical communication with the oil sample for detecting light emitted from the oil sample as the oil sample returns from the excited state to a non-excited state to produce spectral indicia that can be analyzed to determine the presence of fuel in the oil sample.

In accordance with another aspect of the present invention, a method of detecting fuel in oil includes the steps of exposing an oil sample to excitation light in order to excite the oil sample from a non-excited state to an excited state, as the oil sample returns from the excited state to a non-excited state, detecting light emitted from the oil sample and to produce spectral indicia; and analyzing the spectral indicia to determine the presence of fuel in the oil sample.

In accordance with a further aspect of the present invention, a method of detecting fuel in oil includes the steps of: providing an excitation light source for exposing oil sample to light in order to excite the oil sample from a non-excited state to an excited state, and a spectrally selective device for detecting light emitted from the oil sample as the oil sample returns from the excited state to a non-excited state; operating the excitation light source to expose the oil sample to excitation light in order to excite the oil sample from a non-excited state to an excited state; operating the spectrometer to detect light emitted from the oil sample as the oil sample returns from the excited state to a non-excited state to produce spectral indicia; and analyzing the spectral indicia to determine the presence of fuel in the oil sample.

BRIEF DESCRIPTION OF THE DRAWINGS

FIG. 2b is a schematic illustration of an example of a fiber optic probe suitable for use with the spectrographic system shown in FIG. 2a.

FIG. 2c is a schematic illustration of an alternate example of a detection fiber optic bundle suitable for use with the spectrographic system shown in FIG. 2a.

Figure 1:
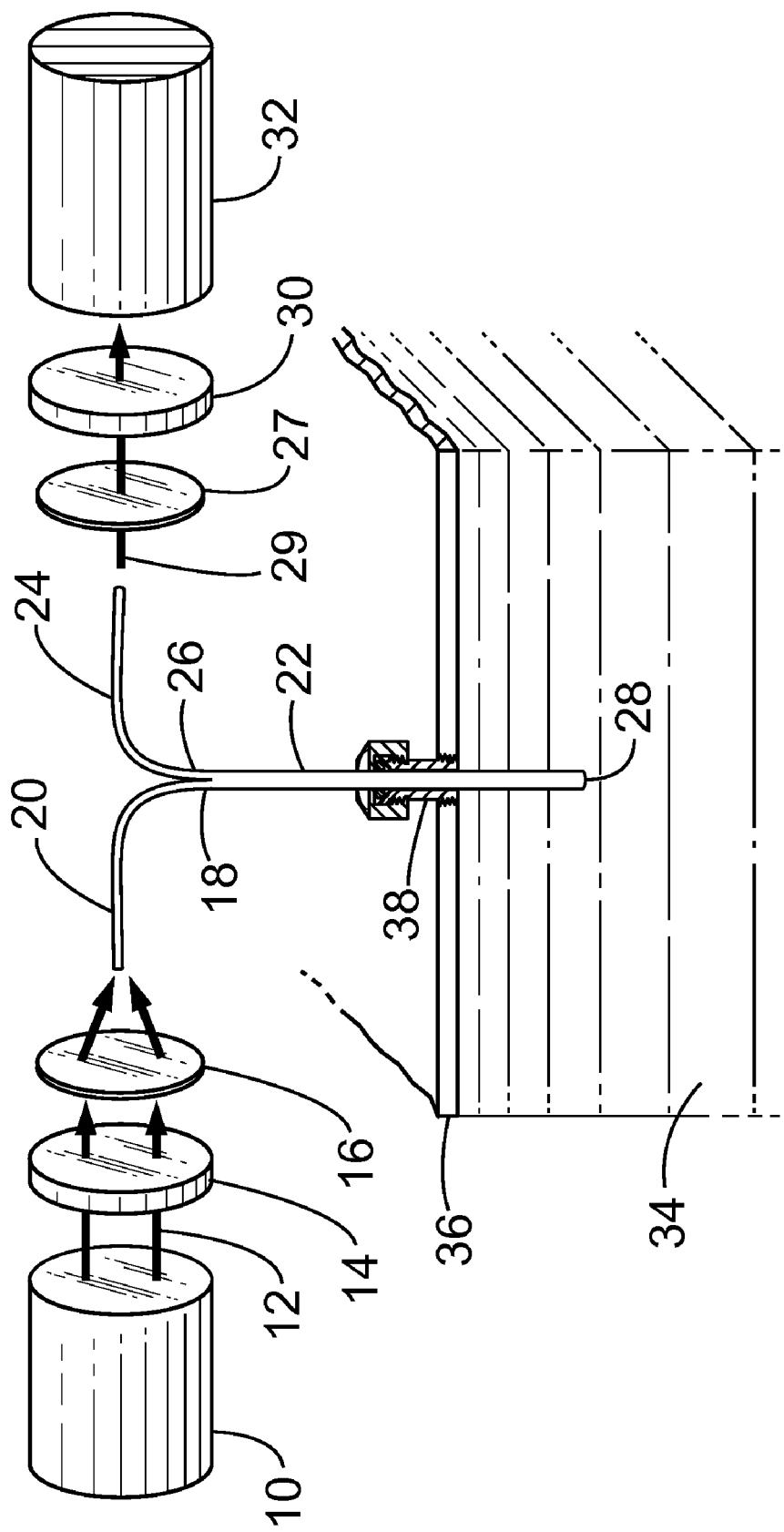
FIG. 1 is a schematic illustration of an example of a spectrographic system suitable for carrying out the present invention.

For a better understanding of the present invention, together with other and further objects, advantages and capabilities thereof, reference is made to the following disclosure and appended claims in connection with the above-described drawings.

DETAILED DESCRIPTIONS OF EXAMPLES OF THE INVENTION

Spectrographic System

In accordance with the present invention, spectroscopy is performed by exciting the state of a sample of interest then detecting the light that is emitted from the sample as the sample returns from the excited state to a lower energy level. The skilled artisan will recognize upon reading the present disclosure that various devices can be used as excitation light sources, for example, light emitting diodes (LED), laser diodes, non-diode laser devices such as gas lasers for example, incandescent devices, fluorescent devices, and the like. The skilled artisan will further recognize that light emitted by a sample may be fluorescent, phosphorescent, Raman, and/or the like. The skilled artisan will further recognize that any of various spectrally selective devices can be used to detect the light emitted by a sample, including a spectrometer, band-pass filters, interferometers, etalons, and the like.

Laser-induced fluorescence (LIF) is an example of a suitable spectroscopic method of carrying out the present invention. Lasers are particularly well suited for the excitation process due to their relatively high power and narrow linewidth. The fluorescence light emitted from the sample is lower in energy than the excitation photon; thus, the fluorescent spectrum of light is Stokes shifted to longer wavelengths relative to the incident excitation wavelength. Since the energy distribution of states is unique for different chemical species, the distribution and magnitude of emitted light (the LIF spectrum) is unique to a chemical species as well.

In comparison to other spectroscopic techniques (such as mid-infrared absorption spectroscopy), LIF spectroscopy generally has a higher signal magnitude and, greater temporal resolution. Since the LIF light signal magnitude decays after excitation, the invention can be employed for in-situ analysis with pulsed lasers and temporally gated spectral detection to effectively specify the exact time in an engine cycle of the measurement. LIF spectroscopy can also be employed in a different optical geometry than transmission absorption spectroscopic methods. For the measurement of oil chemistry, particulate matter in soot and other particulates present in the oil can greatly limit the transmission of light in near- and mid-infrared spectroscopy; however, the invention can be applied so that the incident (excitation) and emitted (fluorescent) light are launched to and received in close proximity from a relatively small oil surface which offers great advantages when collecting light from particulate laden oil samples.

Soot in the oil sample is highly adsorbing and can, therefore, limit the amount of backscattered excitation light from the probe-sample interface due to the high absorbance of the sample. Moreover, changes in the fluorescent signal due to soot content may be used to determine the amount of soot in the oil which is of interest in some applications.

Changes in oil temperature induce changes in the fluorescent signal that can be used to measure oil temperature by calibration of the fluorescent signal changes. Moreover, errors in analysis can be corrected by separately measuring oil temperature and analyzing the fluorescent signal based on both the light spectrum and oil temperature inputs.

A dye, for example a fluorescent dye or a phosphorescent dye, can be added to the fuel to augment the light signal emitted from the fuel, enhancing the signal-to-blank ratio of fuel in oil.

The skilled artisan will recognize, upon reading this entire disclosure, that many if not all of the well-known, conventional various light sources available for fluorescence spectrographic analysis can be used to carry out the present invention, but with varying degrees of precision. The skilled artisan will further recognize that one may select a light source that provides the desired excitation with an optimized signal-to-noise ratio and/or signal-to-blank ratio, and is of reasonable cost. Diode lasers are good examples because they produce light generally at a single wavelength. A variety of excitation energies (light wavelengths) can be used in LIF spectroscopy of oil samples.

During development of the present invention, three examples of light sources were investigated: a 405-nm laser diode, a 450-nm light emitting diode, and a 532-nm laser diode. Although all three light sources were found to be suitable for generating LIF spectra of the oil, fuel, and fluorescent dye tested, in some examples of the present invention the 532-nm light source provided the best signal-to-blank ratio (SBR). Table 1 shows SBR of the dye fluorescence magnitude to the oil fluorescence magnitude for different wavelengths of excitation.

TABLE 1

| | Wavelength | | |
|---|---|---|---|
| | 405 | 450 | 532 |
| SBR* | 16 | 18 | 47 |

*Ratio of dye in fuel fluorescence signal magnitude to oil signal magnitude at 546 nm The LIF method of the present invention detects the fluorescent light signal emitted by both the oil and the dye in the fuel that has entered the oil sample. Thus, the collected light signal is a mixture of the dyed-fuel and oil fluorescence. The detection sensitivity is, thereby, a function of the ratio of the magnitude of the fluorescence signals from the dyed fuel to the oil. The greatest sensitivity for fuel in oil detection will be for cases where the dye fluorescence magnitude is high relative to the oil fluorescence magnitude.

It is important to note that the relative magnitude of the dye and oil fluorescence signals is dependent on the excitation wavelength. In some examples of the present invention it was discovered that excitation with 532-nm light gives a much higher ratio of dye to oil fluorescence than for lower excitation wavelengths of 405 and 450 nm. Table 1 shows the relative magnitude of the dye in fuel fluorescence signal to the signal of oil. In some examples of the present invention the best sensitivity of the technique occurs for the 532-nm excitation as compared with the lower wavelength excitation sources. Furthermore, soot in the oil absorbed the excitation and fluorescent signals more effectively at the lower excitation wavelengths; so, the higher excitation wavelength of 532 nm may also be less susceptible to problems associated with light signal adsorption by soot. Moreover, 532-nm optics are relatively inexpensive due to a plentiful supply of optics at 532 nm for Nd:YAG (a common laser) applications. Therefore, the 532-nm laser diode was selected as a detailed example.

The excitation light can be passed through a bandpass filter to remove any other wavelength of light possibly emitted by the excitation light source. Collimating optics can also be used to focus the light. The skilled artisan will recognize that filters, collimating optics, and the like can be applied to the excitation light path.

An optical communication device is generally but not necessarily interposed between the excitation light source and the oil sample for transmitting excitation light from the excitation light source to the oil sample. Moreover, an optical communication device is generally but not necessarily interposed between the spectrometer and the oil sample for transmitting fluorescence light from the oil sample to the spectrometer.

The excitation light may be launched in direct optical communication or via at least one optical communication device into the motor oil sample. In some examples of the present invention it was found to be convenient to use an optical fiber, for example. Likewise, detection light emitted from the motor oil sample may be launched in direct optical communication or via at least one optical communication device into a spectrometer In some examples of the present invention it was found to be convenient to use an optical fiber, for example. An excitation optical fiber may have a first terminus in optical communication with the excitation light source and a second terminus configured for optical communication with the oil sample. Moreover, a detection optical fiber may have a first terminus configured for optical communication with the oil sample and a second terminus in optical communication with the spectrometer. The skilled artisan will recognize that other known optical communication devices can be used alone or in combination, such as lenses, mirrors, splitters, windows and the like.

Spectral measurement can be carried out using any suitable spectrometer that is sensitive to the wavelength(s) of light that are of interest. Detection light emitted from the motor oil sample can be passed through a 532-nm cut-off, long-pass filter, for example, to remove as much of the reflected excitation light signal as possible prior to entering the spectrometer. The skilled artisan will recognize that filters and other optics can be applied to the detection light path.

A fluorescent light detection system may be comprised of a spectrometer that disperses the light based on the wavelength of light, or a spectrometer that disperses the light based on other means. Moreover, a fluorescent light detection system may be comprised of a series of detectors with bandpass filters to select specific wavelength regions of the fluorescent light signal. Moreover, a fluorescent light detection system may be comprised of a system where the ultimate detection of light is performed by any number of a variety of detectors including, but not limited to, photomultiplier tubes, diode detectors, charge coupled device (CCD) arrays, diode arrays, and the like.

The skilled artisan will recognize, upon reading this entire disclosure, that the method of the present invention is applicable to any oil samples, including: in-situ, for example, oil in any running or non-running engine; and ex-situ, for example, as a drawn sample from any running or non-running engine, or any other source of oil that my be subject to fuel dilution. The skilled artisan will further recognize that the method of the present invention is applicable to a variety of oil/fuel mixtures and chemistries. The skilled artisan will further recognize that the method of the present invention can be applied to measure many oil characteristics including temperature, soot condition, moisture content, and the like.

An example of a spectrographic system suitable for carrying out the present invention is shown in FIG. 1. A 532-nm laser diode 10 produces a beam of light 12 that passes through a 532-nm bandpass filter 14, a collimating lens 16, and into a splitter fiber optic assembly 18, also known as a "splitter probe". The splitter fiber optic assembly 18 comprises two optical fibers 20, 24 that are combined into one common fiber 22 in a "Y"-type configuration; it has an excitation leg 20, a common leg 22, and a detection leg 24. In the example shown in FIG. 1, the probe 28 is inserted into motor oil 34 through a sump enclosure 36 via a fitting 38.

In the example shown in FIG. 1, excitation light 12 is launched into the excitation leg 20 which guides the light 12 to the common leg 22 at a connection point 26. The terminus of the common leg 22 serves as a probe 28. The fluorescent signal at the probe 28 is guided back through the common leg 22, coupled into the detection leg 24, and, shown by arrow 29, guided through a collimating lens 27, a long-pass filter 30 and a spectrometer 32.

Figure 2A:
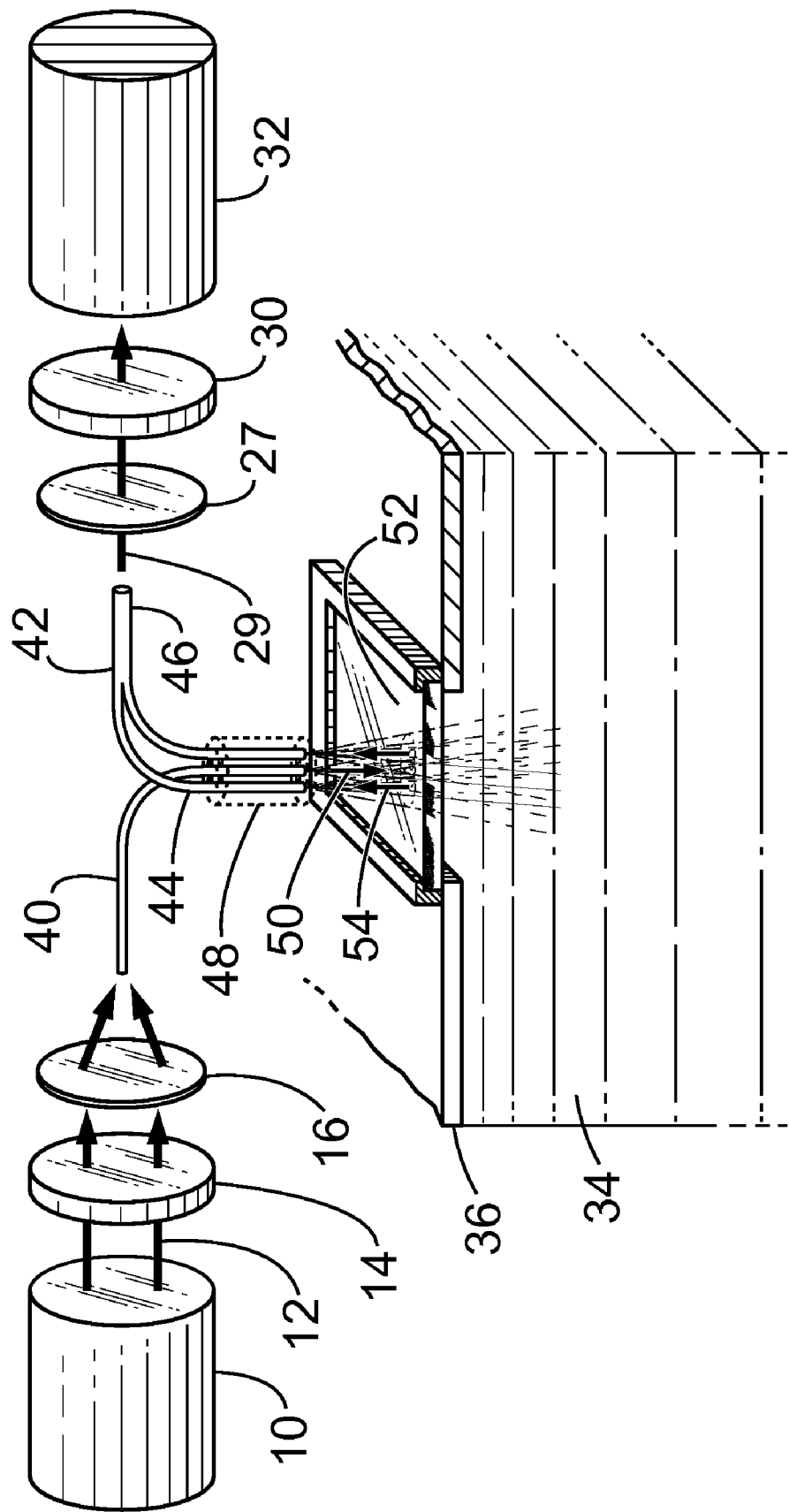
FIG. 2a is a schematic illustration of another example of a spectrographic system suitable for carrying out the present invention.
Figure 2C:
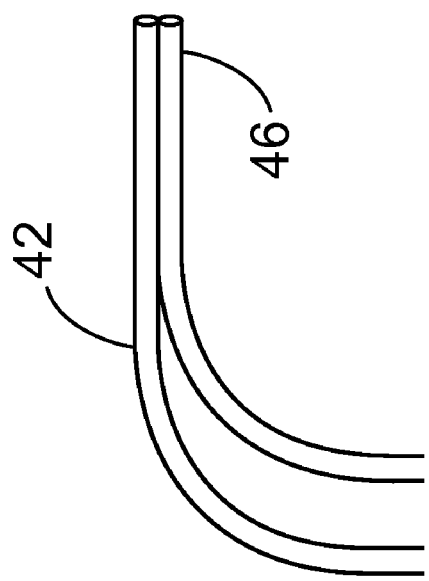
Figure 2B:
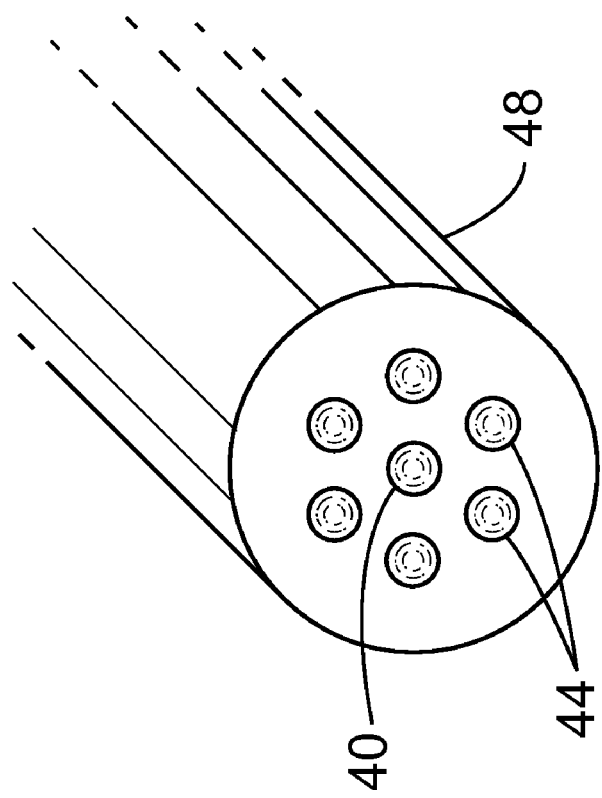

Another example of a spectrographic system suitable for carrying out the present invention is shown in FIGS. 2a, 2b. A 532-nm laser diode 10 produces a beam of light 12 that passes through a 532-nm bandpass filter 14, a collimating lens 16, and into an excitation optical fiber 40.

FIG. 2b shows an end-view of an example of a probe 48, referred to as the "6-around-1" probe. A single excitation optical fiber 40 is surrounded by six individual detection optical fibers 44. The number of excitation optical fibers and individual detection optical fibers can be varied. Other examples of suitable probes are those that have a plurality of excitation optical fibers and a single detection optical fiber, those that have a single excitation optical fiber and a single detection optical fiber, and those that have a plurality of excitation optical fibers and a plurality of detection optical fibers.

In the example shown in FIG. 2a, a detection optical fiber assembly 42 comprises a plurality of individual detection optical fibers 44 that are fused into one common detection optical unit 46. FIG. 2c shows another example where the detection optical fiber assembly 42 comprises a plurality of individual detection optical fibers 44 that are bundled into one common detection optical unit 46. The common detection optical unit 46 can be a simple bundle of optical fibers or an array of optical fibers.

In the example shown in FIGS. 2a, 2b, 2c, excitation light 12 is launched into the excitation optical fiber 40 which guides the light 12 to the probe 48 where the excitation light is emitted as a conical excitation beam 50. In this example, a transparent window 52 is used to allow the probe 48 to be placed at a sufficient distance from the motor oil 34 for overlap of the conical excitation beam 50 and conical emission zones 54 of the individual detection optical fibers 44. The fluorescent signal at the probe 48 is guided back through the individual detection optical fibers 44, the common detection optical unit 46, and, shown by arrow 29, guided through a collimating lens 27, a long-pass filter 30 and a spectrometer 32.

The probe 28, 48 may be positioned to sample the cylinder wall oil in order to allow measurement of oil with higher fuel content. Examples of sample positions include the cylinder wall proper and a position below the cylinder that contains oil scraped down off of the cylinder by the piston ring pack. The probe 28, 48 may be simply inserted into motor oil ex-situ, or in-situ where, for example, the probe 28, 48 is inserted into an engine, an oil line, oil filter, or the like.

Both probes described hereinabove produce essentially the same spectra, with varying amounts of back scattering and other noise. Although measurements were successfully made with both probes, the 6-around-1 probe gave a better overall signal-to-noise level due to the lower amount of backscatter laser light detected. Examples below were performed using either or both of the spectrographic systems described herein.

Chemistry and Calibration

The collected detection light contains both light emitted by the oil in the sample and light emitted by the fuel or dyed fuel, enabling quantification of the amount of fuel relative to the oil (a concentration measurement). This offers advantages against other effects that may occur during signal collection. As excitation light signal varies, fluorescent light signal varies also, but generally by the same amount for all analyte species. Therefore such variations have minimal affect on the ratio of fuel to oil fluorescence. Moreover, as particulate matter (soot, for example) levels in oil vary, fluorescent light signal varies also, but generally by the same amount for all analyte species. Therefore such variations have minimal affect on the ratio of fuel to oil fluorescence.

The skilled artisan will recognize that quantification can be accomplished with simple ratio techniques (ratio of spectral regions, for example) or more complicated analysis techniques that utilize spectral signatures for improving detection and sensitivity.

In accordance with some examples of the present invention, a fluorescent dye can be added to the fuel in order to increase the amount of fluorescent light and thereby increase the sensitivity of the technique to fuel in the motor oil, especially at low concentrations. Although fuel itself can give a fluorescent light signal, addition of a dye can increase the sensitivity of the method. The dye can have a unique fluorescent spectral signature (intensity vs. wavelength of light emitted) that enables the dye to be better differentiated from the oil fluorescence so that signals at lower levels can be accurately measured. Moreover, the dye can have a larger fluorescent signal relative to the fuel which increases the ability to quantify the fluorescent signal at lower levels.

Generally speaking, liquid petroleum fuels are a complex mixture of hydrocarbon-based chemistry; the dye chemistry is more specific, providing an advantage for tracking dye fluorescence over time in the engine and oil system.

Commercially available dyes manufactured for detecting leaks in engine systems are suitable for carrying out the present invention. Such dyes are generally convenient because they are readily available and have been designed for engine use. The dyes are compatible with engine systems and do not cause any damage to the engine parts. Moreover, such dyes are generally cost effective since a market already exists for their use. Moreover, such dyes have been studied for safety, have known safety procedures, and are generally safe to use.

An example of a suitable, commercially available leak detecting dye of diesel fuel and oil systems is Dye-Lite® TP-3400, a registered trademark owned by Tracerline Products, a subsidiary of Spectronics Corporation, 956 Brush Hollow Road, Westbury, N.Y. 11590. Referred to hereinafter as "dye", the dye was selected for testing in examples of the present invention. Dye can be added, for example, at levels of 0.05-0.10% by mass. More or less dye can be added as long as the desired fluorescent effect is achieved, but the additive level should not be so high as to adversely affect combustion or lubricant properties to a significant extent. Moreover, the dye should be soluble in diesel fuel and motor oil and should be safe for diesel equipment and users.

It is contemplated that other dyes, such as laser dyes, can be used to carry out the present invention.

The skilled artisan will recognize that the invention can be used with any motor oil and any fuel, and with any internal combustion engine, including gasoline engines. The motor oil, fuel, and engine described herein are used as examples.

Figure 3:
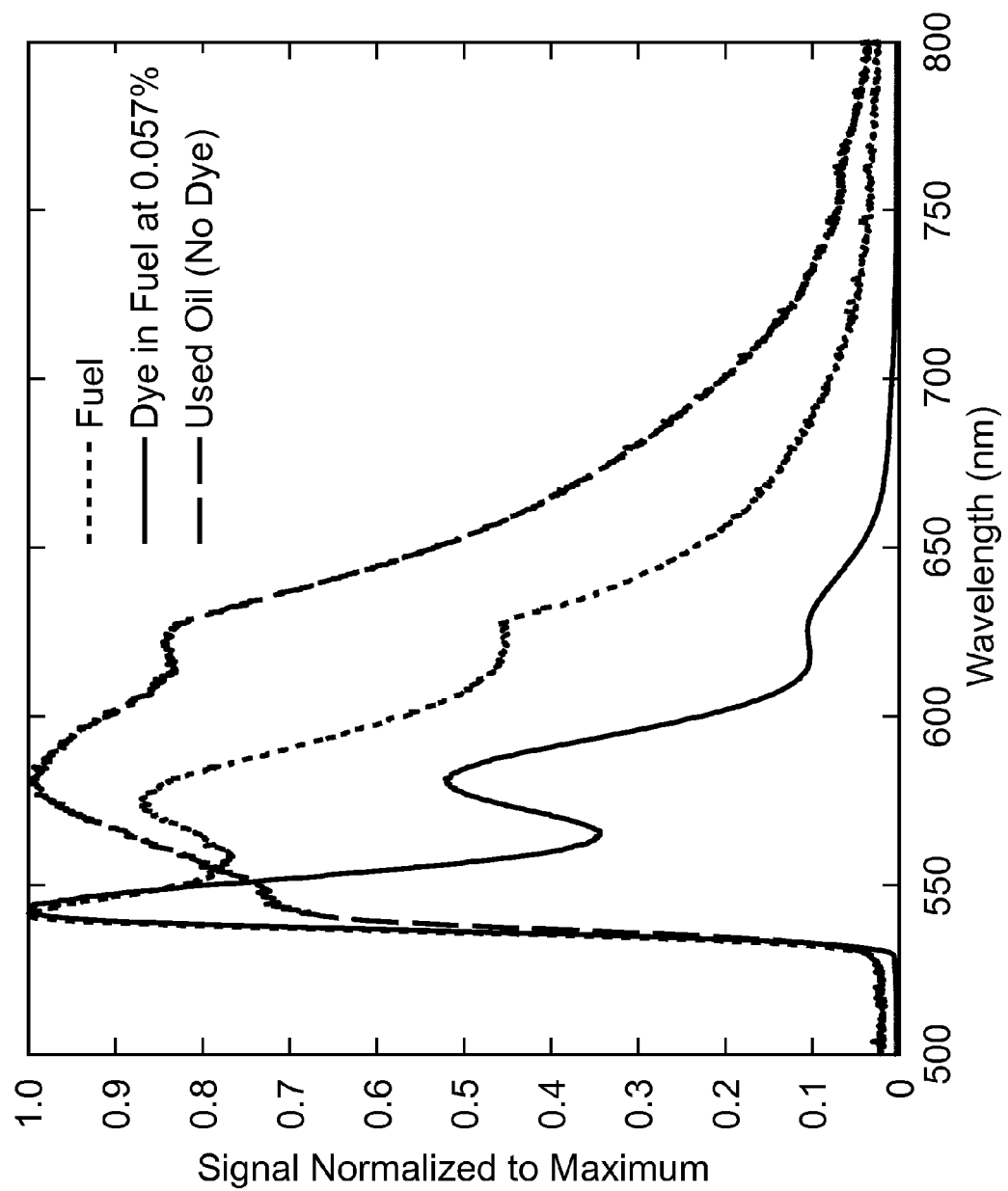
FIG. 3 is a graph showing normalized laser-induced fluorescence (LIF) spectra of diesel fuel, dye, and oil.
Figure 4:
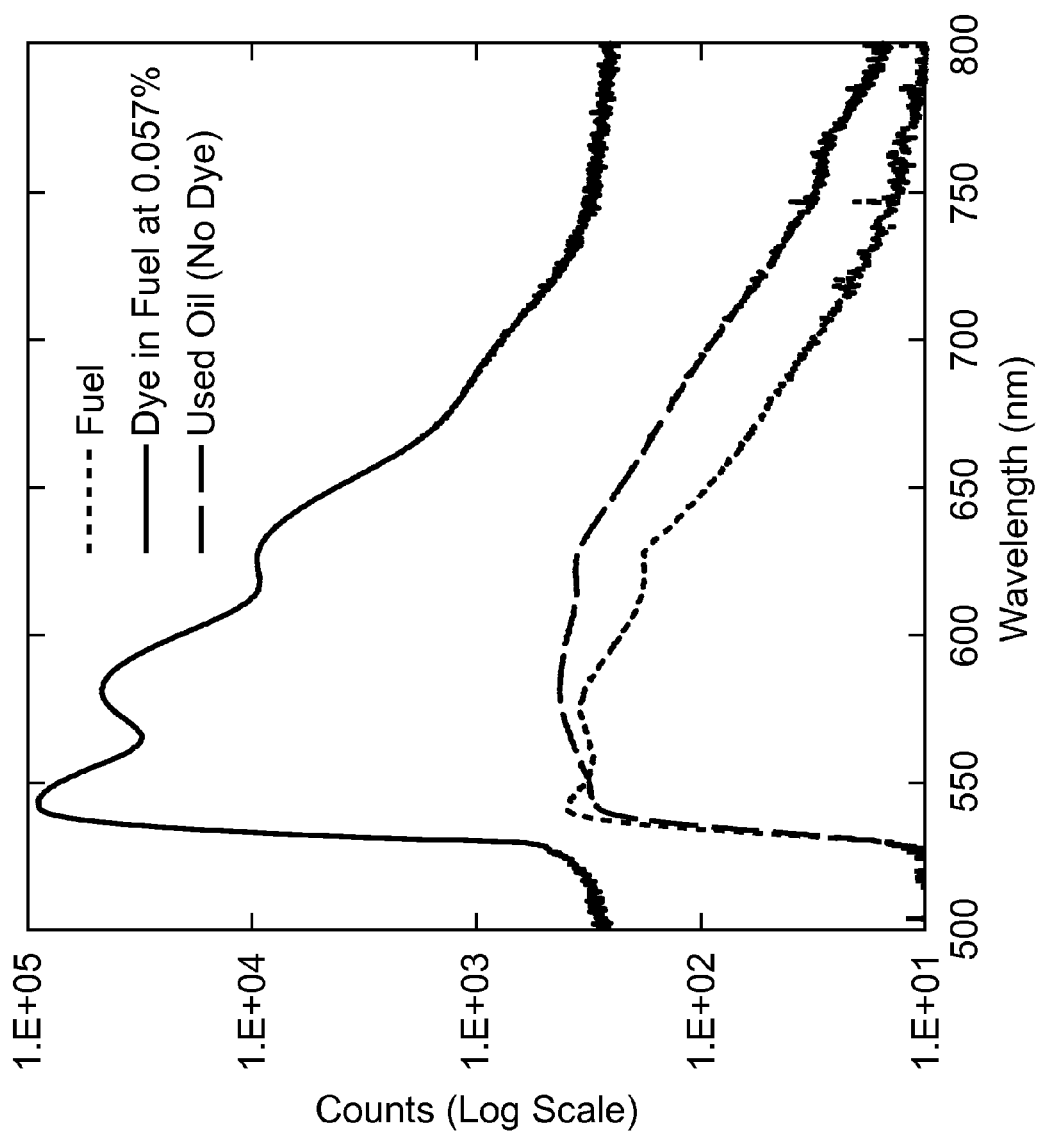
FIG. 4 is a graph showing log scale LIF spectra of diesel fuel, dye, and oil.

Test spectra obtained prior to testing the invention under operating conditions are shown in FIGS. 3, 4. A spectrum was obtained from a sample of used Mobil Delvac 1300. Super Exxon Mobil Corporation, 3225 Gallows Road, Fairfax, Va. 22037) 15W-40 oil. The diesel fuel spectrum was obtained from a sample of the CPChem ultra low sulfur 2007 (a trademark of Chevron Phillips Chemical Company, LLC, 10001 Six Pines Drive, The Woodlands, Tex. 77380) certification fuel sample. The dye was mixed into the diesel fuel at a level of 0.057% by mass to obtain the third spectrum. For comparison, the spectra in FIG. 3 have been normalized to their maximum signal. FIG. 4 shows the spectra without normalization and on a log scale. Although the spectral features are relatively broad in nature, there is a clear distinction between the relative spectral shapes of the three samples. In particular, the dyed fuel sample spectrum contains the largest LIF signal at ~540 nm with much smaller features at 580 nm and 625 nm. In contrast, the oil spectrum is relative broad with a peak LIF signal at 580 nm.

Although the normalized fuel spectrum shown in FIG. 3 appears to be between the oil and dyed fuel samples, the actual magnitude of the fuel LIF signal is smaller than both the oil and dyed fuel samples as shown in FIG. 4. Furthermore, the dyed fuel sample LIF magnitude is much greater than both the oil and fuel sample spectra. Table 2 shows the maximum LIF spectrum signal level for the samples shown in FIGS. 3, 4; in addition, the maximum signal level for a used oil sample is shown for comparison. Soot in the used oil sample is responsible for the reduced LIF signal level.

TABLE 2

| Sample | Peak LIF Signal (Counts/msec) |
|---|---|
| Oil (fresh) | 27 |
| Oil (used) | 5 |
| Fuel | 4 |
| Fuel + 0.057% Dye | 1003 |

Figure 5:
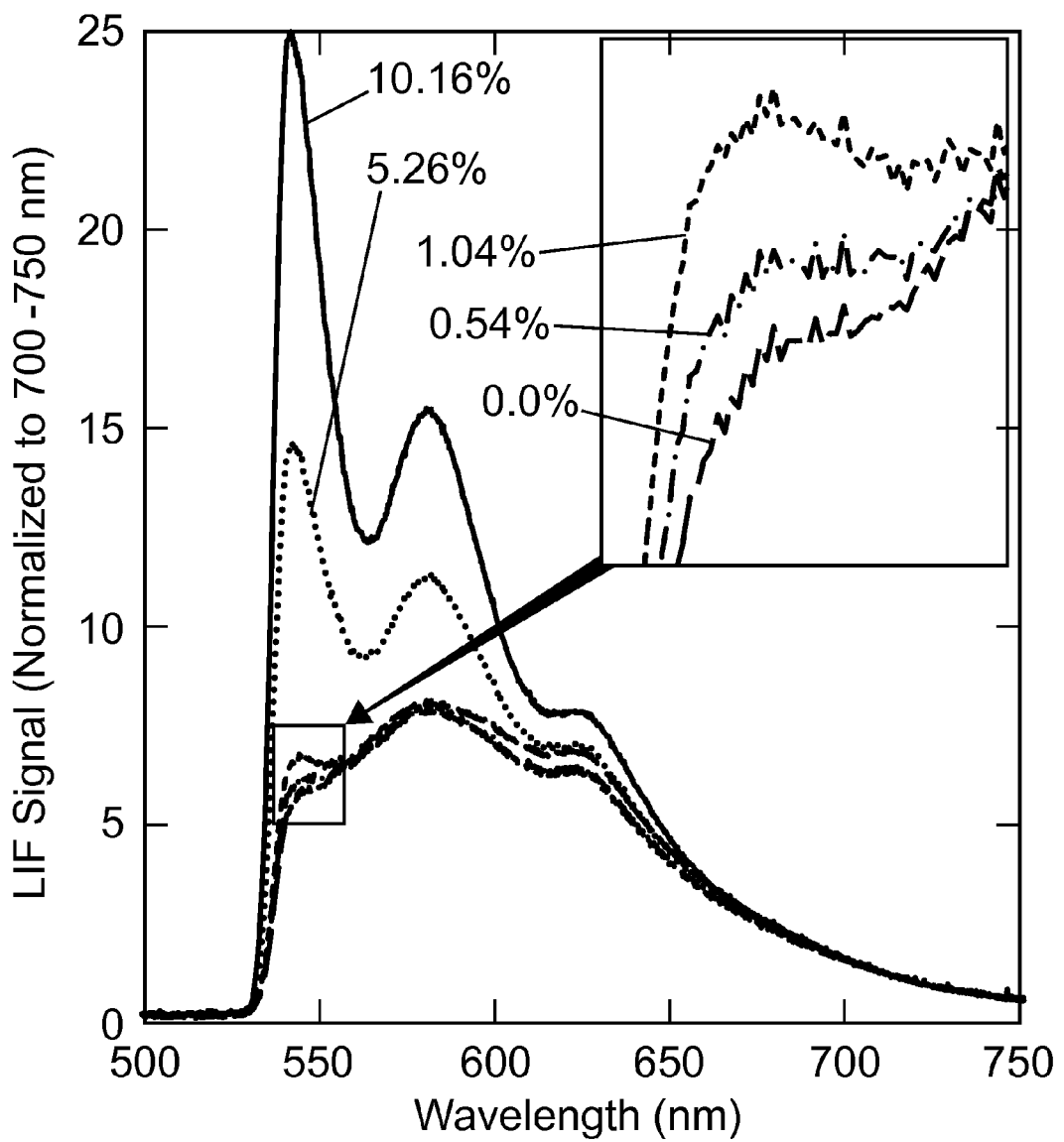
FIG. 5 is a graph showing LIF spectra of some calibration standards based on used oil and dyed fuel mixtures.

In order to quantify the LIF spectra obtained during engine experiments, a set of calibration standards were created and analyzed at room temperature using the fiber optic probes. Used oil was mixed with the dyed fuel standard (0.057% by mass dye in fuel) to create the calibration standards. FIG. 5 shows LIF spectra of some of the calibration standards. The concentration values indicated on the plot represent the level of fuel in the oil. The spectra have been normalized to the average counts in the spectral region from 700-750 nm in order to compensate for variations in overall signal intensity due to drift in the laser power. The 0% standard represents the LIF spectra of oil only. As the concentration of dyed fuel increases in the standards, increases in the 540-nm and 580-nm peaks occur primarily due to the fluorescence of the dye (the fuel fluorescence contribution is a factor of 250 less in magnitude). As shown in the inset, at fuel concentrations below 1%, the increase in the 540-nm peak is still evident, but the signal differences begin to approach the noise level of the spectra.

Figure 6:
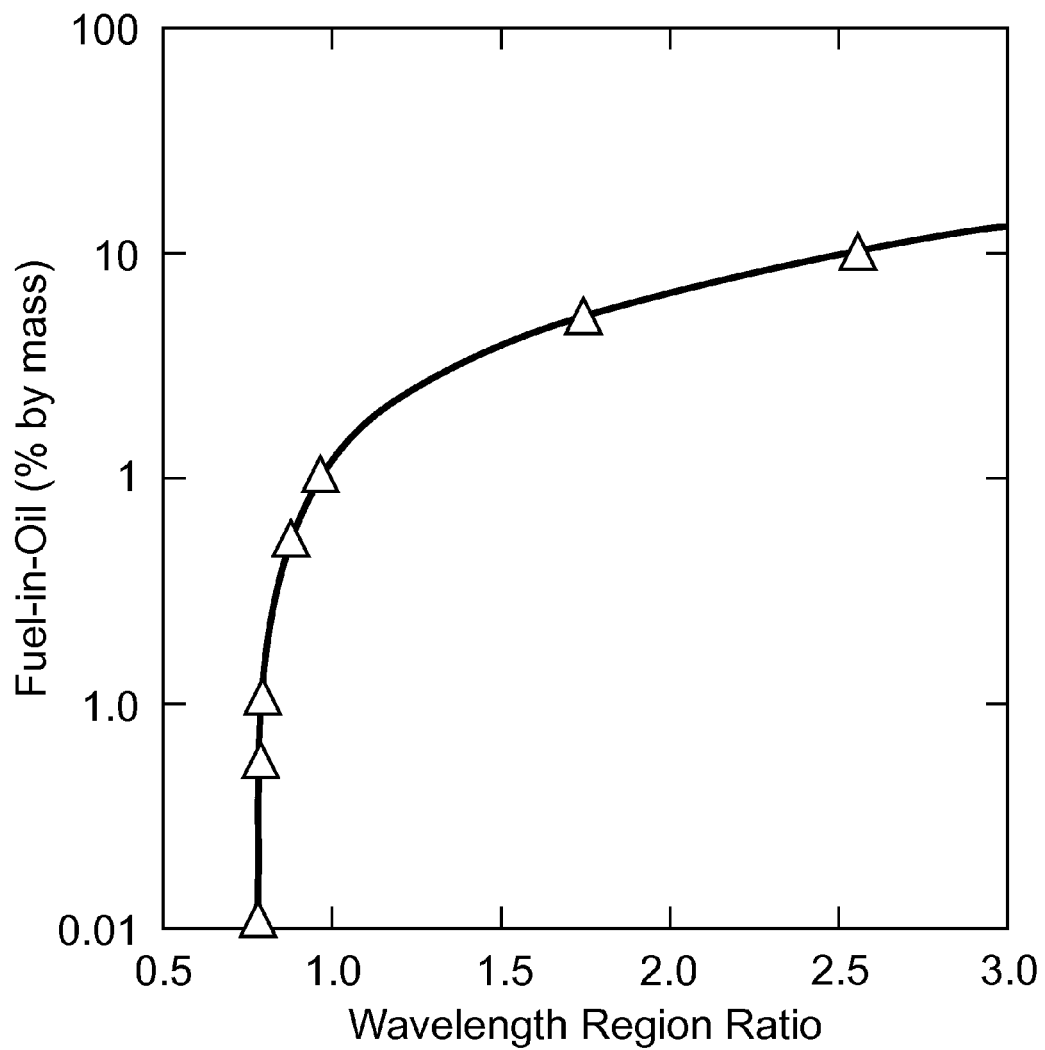
FIG. 6 is a graph showing a calibration curve obtained by relating a known fuel in oil concentration sample to the ratio of two wavelength regions in the LIF spectra.

The shape of the LIF spectra allows the dyed fuel to be detected in the used oil. Increases in the 540 nm and 580 nm peaks relative to the 625 nm peak and the shoulder region between 650 and 750 nm indicate higher dye (and thereby fuel) presence in the oil. To quantify the fuel in oil based on the LIF spectra, the average LIF signal in spectral regions were ratioed to give a quantity that could be related to the fuel content in oil. The best calibration fit was obtained by ratioing the LIF signal in the wavelength region of 535-555 nm (Region I) to the wavelength region of 620-630 nm (Region II). The calibration curve generated with this relationship is shown in FIG. 6; a third order polynomial (correlation coefficient=0.999997) was used to fit the measured data to the known sample fuel in oil levels. An increase in the ratio indicates higher dyed fuel (Region I) content relative to the oil signal (Region II) as expected. As the dyed fuel content approaches levels less than 0.1%, the differentiation of the spectral differences becomes difficult relative to the noise of the LIF signal and the measurement resolution is approached; in practice, the precision of the LIF method allowed changes of +/−0.01% fuel in oil to be detected for 1-minute averaged spectral data. The skilled artisan will recognize that this is one calibration method, used as an example, that other calibration methods may be used, and that such other calibration methods may result in different detection limits.

Another factor impacting the magnitude of the LIF signal is the sample temperature. As temperature increases, the fluorescence quantum yield decreases, in turn decreasing the LIF signal magnitude. The spectral region ratio quantification technique is beneficial in reducing the impact of sample temperature. However, this temperature effect is only perfectly accounted for if the quantum yield variations are the same for both the dye and oil. The variation in quantum yield as a function of temperature for the oil and dyed fuel was not measured. Instead, the calibration obtained at room temperature (25° C.) was used. Since all measurements on the engine platform were made at a constant temperature of 50° C., the results can be expected to be offset by a constant factor attributable to the quantum yield variations; this factor should be close to unity since the delta temperature is only 25° C. Nevertheless, the relative results obtained are valid and give the primary information of interest for rapid measurement of fuel dilution rate for various operational conditions.

Testing for Fuel Dilution of Oil

Development of suitable analytical methods is explained herein in order to elucidate the complex nature of such methods. Experiments with the LIF method for fuel dilution of oil analysis were conducted on a diesel engine mounted on a dynamometer platform. The engine was operated in various lean and rich combustion modes, and the motor oil inside the engine was tested during operation to determine the rate at which the oil was being diluted by fuel. Probes as described hereinabove were installed in an easily accessible oil return line between the engine and oil cooler. Experiments were conducted by operating the engine in a lean-rich cycling mode suitable for NOx-trap catalyst regeneration. The engine was throttled to assist net-rich exhaust. Further details of such testing can be found in Brian West, Shean Huff, James Parks, Sam Lewis, Jae-Soon Choi, William Partridge, and John Storey, "Assessing Reductant Chemistry During In-Cylinder Regeneration of Diesel Lean NOx Traps", Society of Automotive Engineers Technical Paper Series 2004-01-3023 (2004). Testing parameters included controlling fuel injection events in terms of timing, volume, and duration.

Figure 7:
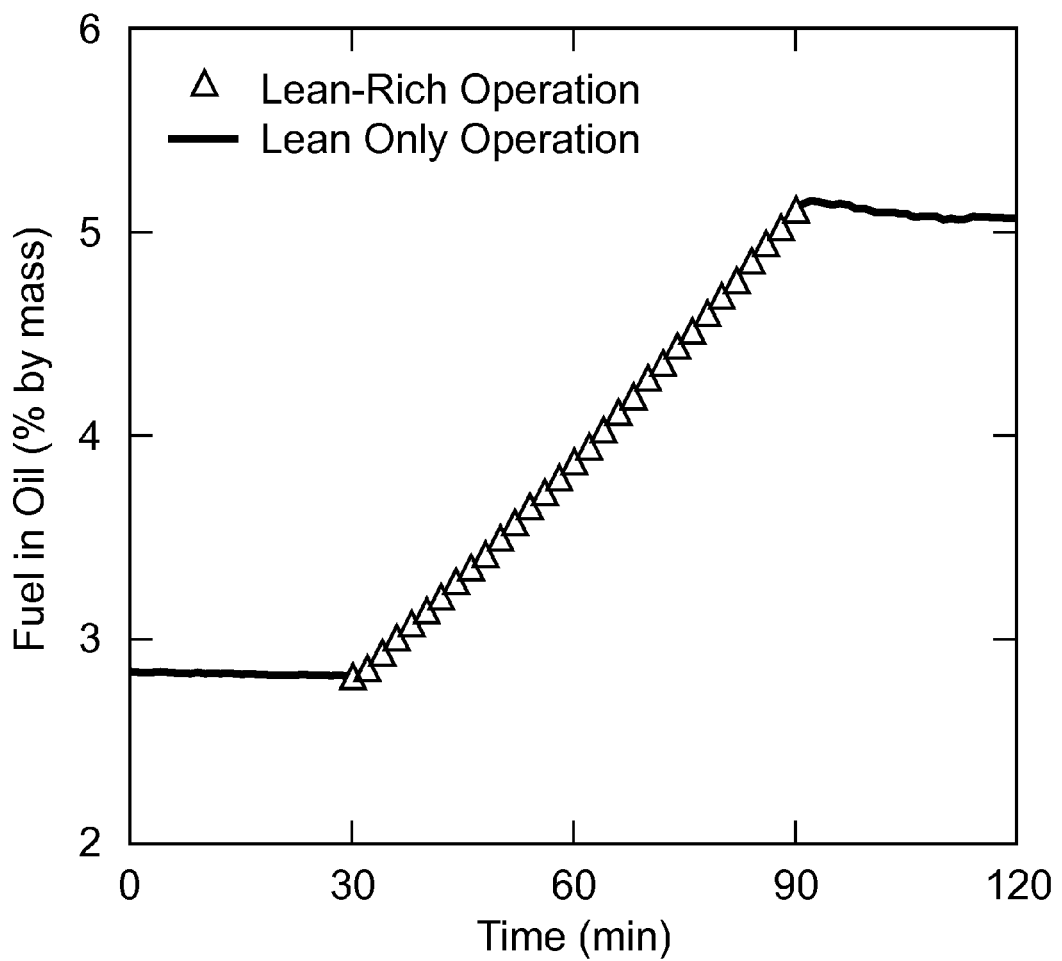
FIG. 7 is a graph showing a LIF spectrum that indicates the accumulation of dye in motor oil over time during lean-rich operation.

As oil dilution is associated with fuel-rich operation the fuel content in oil was analyzed during lean-only and lean-rich operation. FIG. 7 shows the accumulation of fuel in the oil over time during lean-rich operation. The engine was run in lean-only mode for 30 minutes, wherein there was no indication of an increase of fuel dilution of the oil. The engine was run in lean-rich mode for the next 60 minutes, wherein there was a remarkable indication of increased fuel dilution of the oil; in fact the oil dilution rate is practically constant over this lean-rich operation time. The engine was again run in lean-only mode for the next 30 minutes, wherein there was no indication of further fuel dilution of the oil.

The increasing fuel content in the oil was analyzed as a function of the number of regeneration events to determine a fuel dilution rate as a function of regeneration event; this fuel dilution per regeneration was a figure of merit for comparing different regeneration strategies. In general, the increase in fuel content was a linear function of time for the studies presented here; results presented hereinbelow are average slopes of fuel in oil for periods of 15 to 30 minutes of operation at a given lean-rich strategy. At the beginning of the experiment (time=0) in FIG. 7, the reported fuel content in oil was 2.8% which represents the amount of dye in the oil at the beginning of the experiment. In practice, it was found that some amount of dye remained in the oil even after an oil change. Thus, the baseline fuel in oil varies with engine operation history. Therefore, oil dilution effects of specific engine operation strategies must be referenced to the appropriate baseline.

Accumulation of fuel in the oil is tempered by evaporation of that fuel, but the evaporation rate of the dye is so low that the dye accumulates in the oil at a greater rate than does the fuel. It is important to note that the dye entering the engine system with the fuel can follow two pathways once in the system. Either the dye can be combusted with the fuel and exit the system with the exhaust, or the dye can enter the oil film on the cylinder wall. Since the dye goes into solution with the oil, the dye is effectively permanently stored in the oil if the oil route is taken. The dye interactions with the system differ somewhat from the interactions of the fuel. Although the fuel can follow the same pathways as the dye, the fuel can also evaporate from the oil. The amount of fuel evaporating from the oil will vary according the chemistry of the individual fuel components; thus, quantifying the actual fuel concentration in oil is complex and must account for several mechanisms which all may differ with the specific chemistry of the fuel. The purpose of the LIF approach presented here is to provide a rapid means of quantifying the rate of fuel dilution of oil for different engine combustion strategies and accelerate engine control strategy development. Measurement of fuel evolution from the oil is not generally obtained. Moreover, most applications are on time scales where fuel evaporation from the oil is negligible. A complete characterization of the full path of fuel transport into and out of the oil system would require further information relating to fuel distillation and evaporation.

During engine experiments, LIF spectra were nominally recorded every 0.5 to 1 second. Dark noise spectra (electronic noise in the spectrometer detectors) were recorded for the same time period at the end of experimental trials and the dark noise was subtracted from the data during post analysis. Analysis of the spectra for fuel concentration in oil was performed on one-minute averaged spectra based on the calibration relationship shown in FIG. 6.

Figure 8:
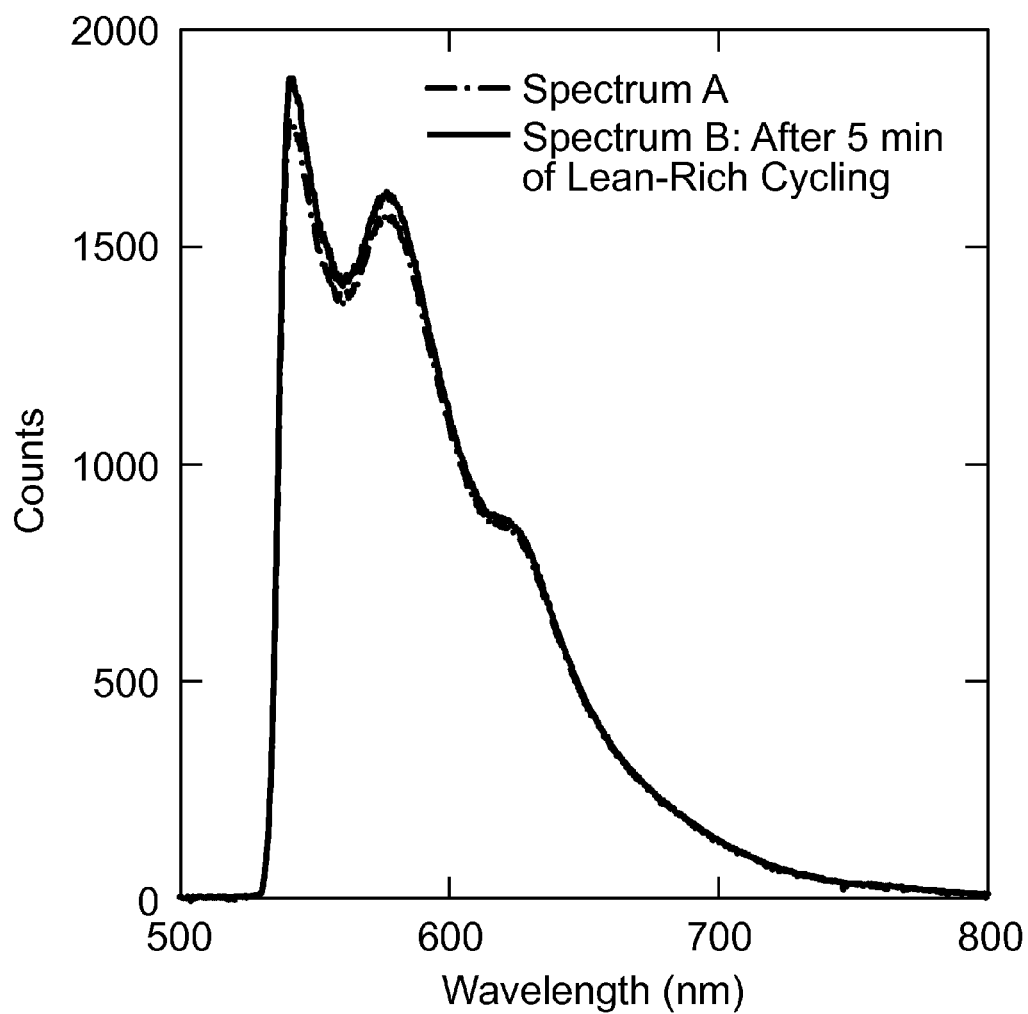
FIG. 8 is a graph showing LIF spectra during engine testing.
Figure 9:
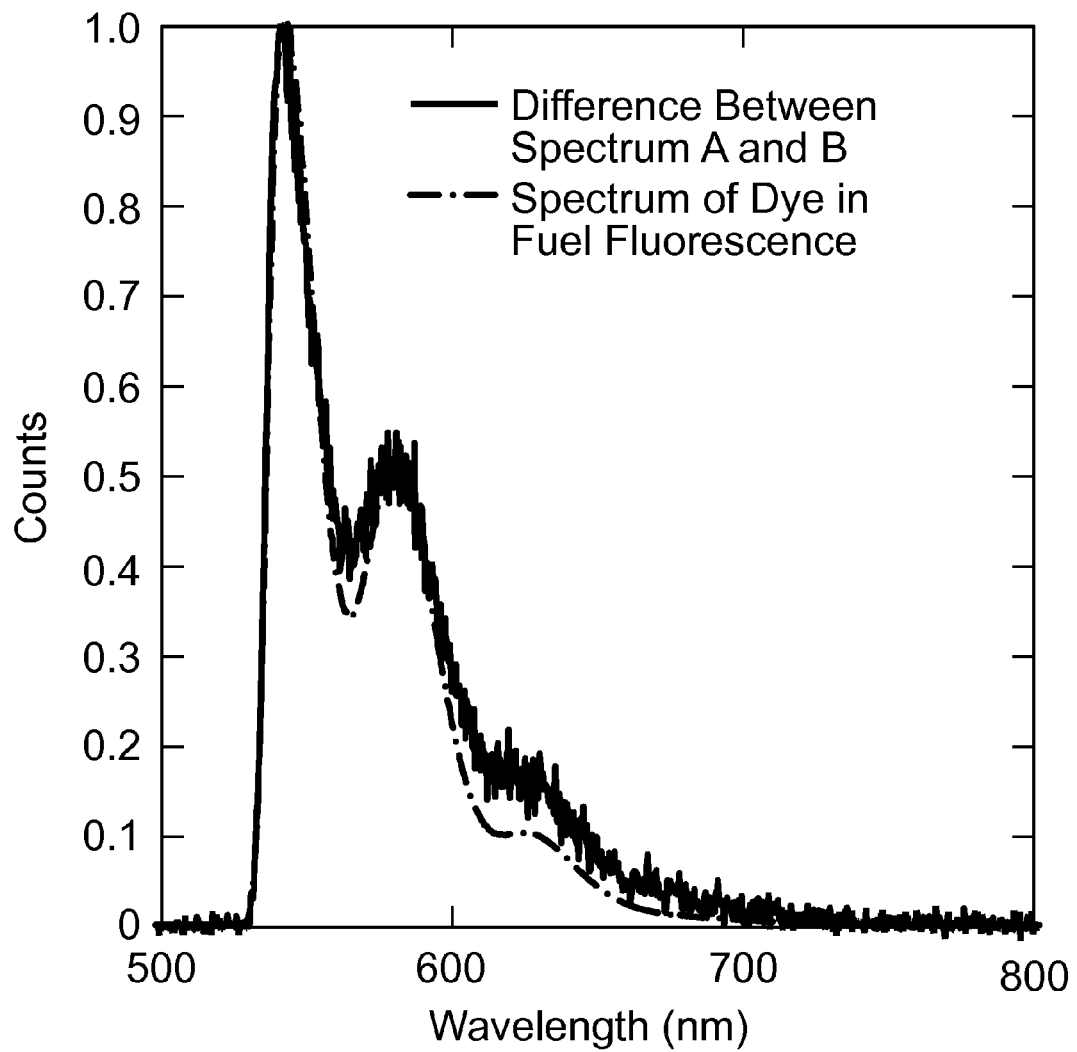
FIG. 9 is a graph showing the dye LIF spectra and the difference in the LIF spectra of FIG. 8.

A pair of example spectra from an engine experiment is shown in FIG. 8; spectrum B was obtained 5 minutes after spectrum A. During this experiment, rich operation was conducted by injection of extra fuel into the engine at 80° past top dead center; the rich period lasted 3 seconds and occurred every 20 seconds. At the time that spectrum A was acquired, some dyed fuel had already penetrated into the oil as indicated by the difference between spectrum A and the spectrum of used oil without any dyed fuel (FIG. 3). After 5 minutes of operation when spectrum B was acquired, an increase in the LIF signal in the 540-nm and 580-nm peak regions is apparent and indicates that more dyed fuel has entered the oil. The difference in the spectra of FIG. 8 is due to the additional dye entering the oil from the rich combustion mode and is apparent by examining the difference between spectra A and B shown in FIG. 9. An LIF spectrum of the dyed fuel is shown for reference in FIG. 9. The difference spectrum obtained from the engine experiment and the dyed fuel spectrum are of the same spectral shape, which verifies that the fluorescence of the dye is being detected.

Figure 10:
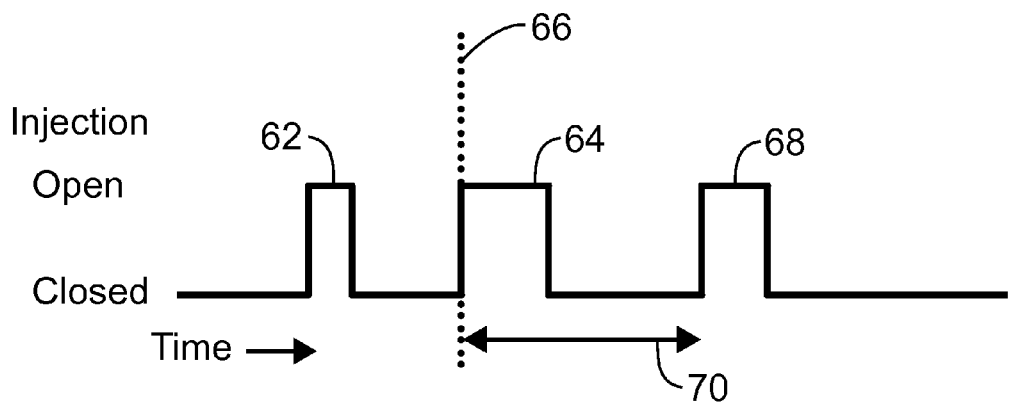
FIG. 10 is a graph illustrating a fuel injector operation cycle for a time sweep experiment.
Figure 11:
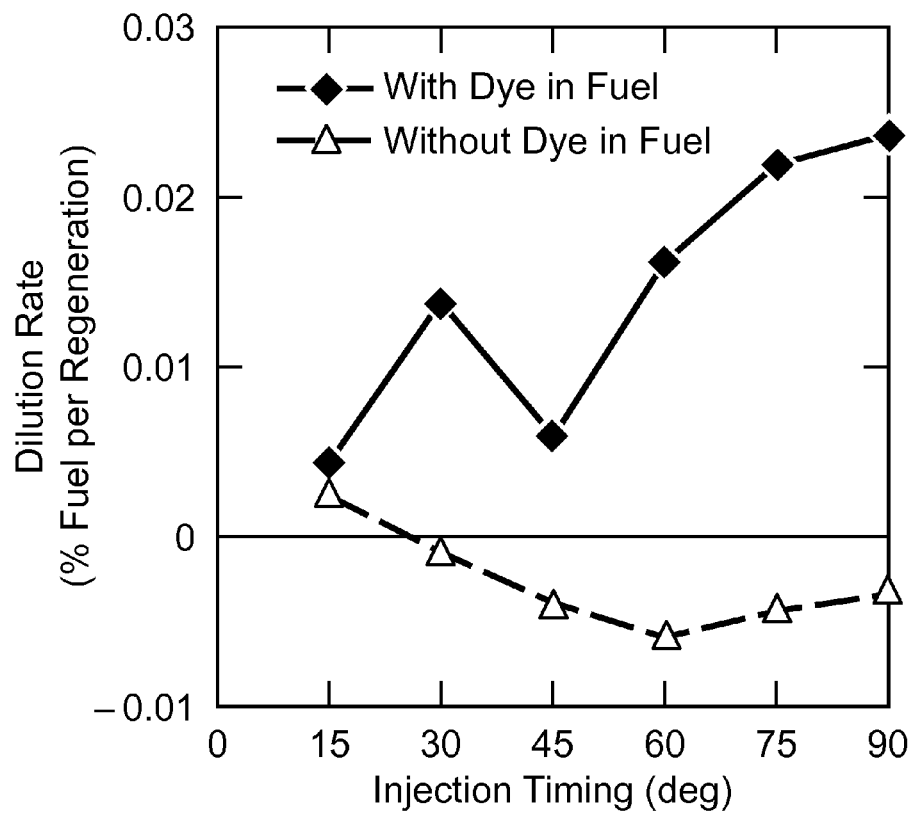
FIG. 11 is a graph showing dilution rate as a function of injection timing for a time sweep experiment.

Timing sweep experiments were conducted in which the timing of the extra fuel injection for rich combustion operation was varied while holding the minimum air-to-fuel ratio during the rich event constant. FIG. 10 shows a fuel injector operation cycle including a pilot injection event 62, a main injection event 64 beginning at top-dead-center (TDC) 66, and an extra injection event 68. The pilot injection event 62 and the main injection event 64 were kept constant, while the timing of the extra injection event 68 varied as shown by an arrow 70. The extra injection event 68 was timed at starting crank angles of 15°, 30° 45°, 60°, 75°, and 90° past top dead center (TDC). The variation in measured oil dilution as a function of the extra-injection's timing is shown in FIG. 11. The fuel dilution increased sharply between the 45° and 60° timing points. In general, the dilution increased with increasing injection delay; however, interestingly, the 30° timing point displayed a local maximum for fuel dilution. The experiment was also performed with no dye present in the fuel, showing that detection of oil dilution by fuel is dependent on the dye component in the fuel at this level.

Figure 12:
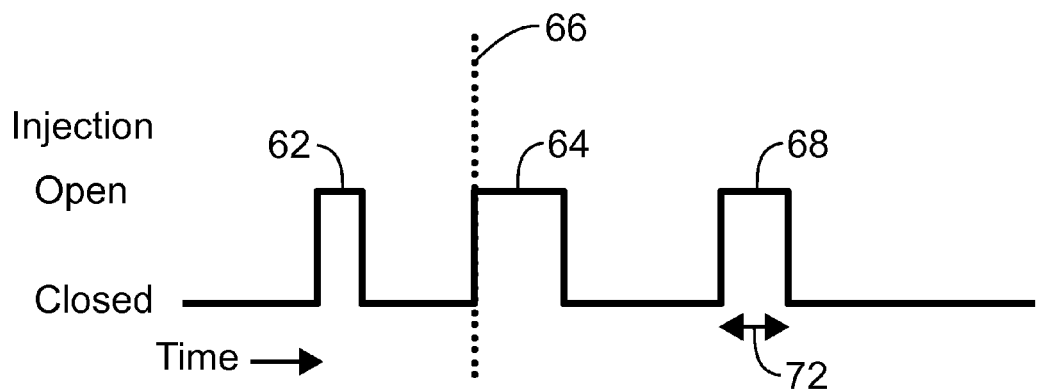
FIG. 12 is a graph illustrating a fuel injector operation cycle for an air-to-fuel ratio experiment.

Air-to-fuel ratio experiments were conducted in which the timing was held constant while the minimum air-to-fuel ratio was varied. An objective of the experiments was to characterize fuel dilution as a function of minimum air-to-fuel ratio during the rich combustion mode. Air-to-fuel ratio can be controlled by throttling intake air, adding fuel with additional in-cylinder fuel injection, or a combination of the foregoing. The experiment was conducted by two techniques. The first technique was to hold the throttle value constant while varying the amount of fuel injected, indicated in FIG. 12 by arrow 72. The second technique was to vary the throttle while holding the fuel injection amount constant. For both techniques, the timing of the additional fuel injection was held constant at 60°.

Figure 13:
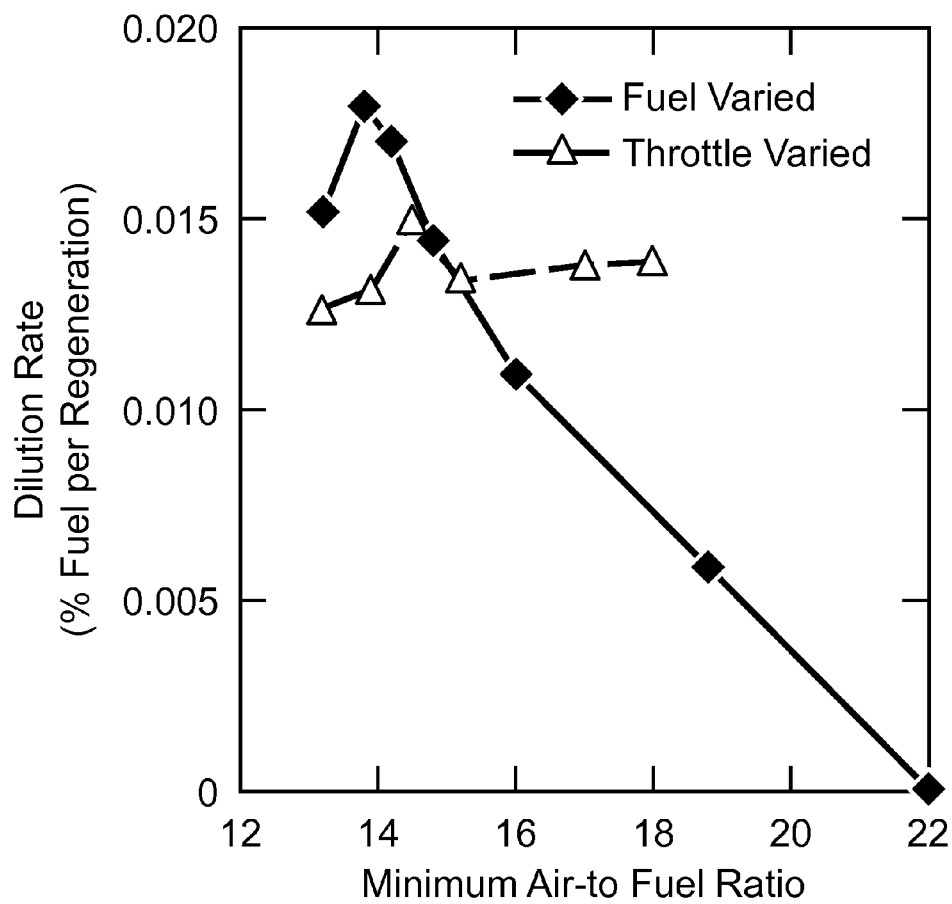
FIG. 13 is a graph showing dilution rate as a function of minimum air-to-fuel ratio for an air-to-fuel ratio experiment.

FIG. 13 shows the results from both techniques employed to vary the air-to-fuel ratio. For the case where throttling was varied while additional fuel injection was held constant, relatively little change was observed in the fuel dilution as a function of air-to-fuel ratio. The small trend observed indicated that fuel dilution slightly increases with higher minimum air-to-fuel ratio; thus, increased air charge in the cylinder may deter some fuel from entering the cylinder wall oil film.

When varying air-to-fuel ratio by adjusting fueling rate while holding the throttle constant, the fuel dilution rate changed much more dramatically as a function of air-to-fuel ratio, as shown in FIG. 13. As fueling rate increased to achieve lower air-to-fuel ratios, the fuel dilution rate increased.

Figure 14:
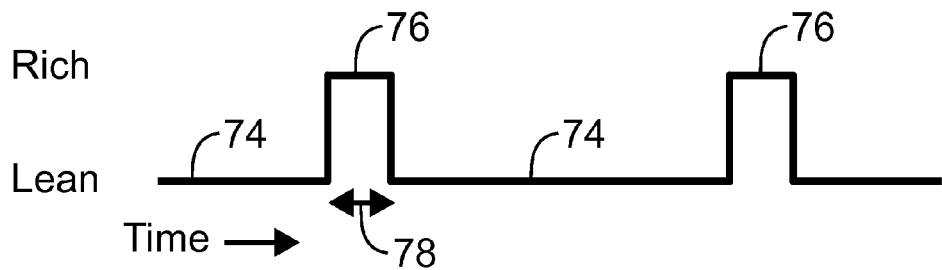
FIG. 14 is a graph illustrating rich and lean operation cycles for a rich duration experiment.
Figure 15:
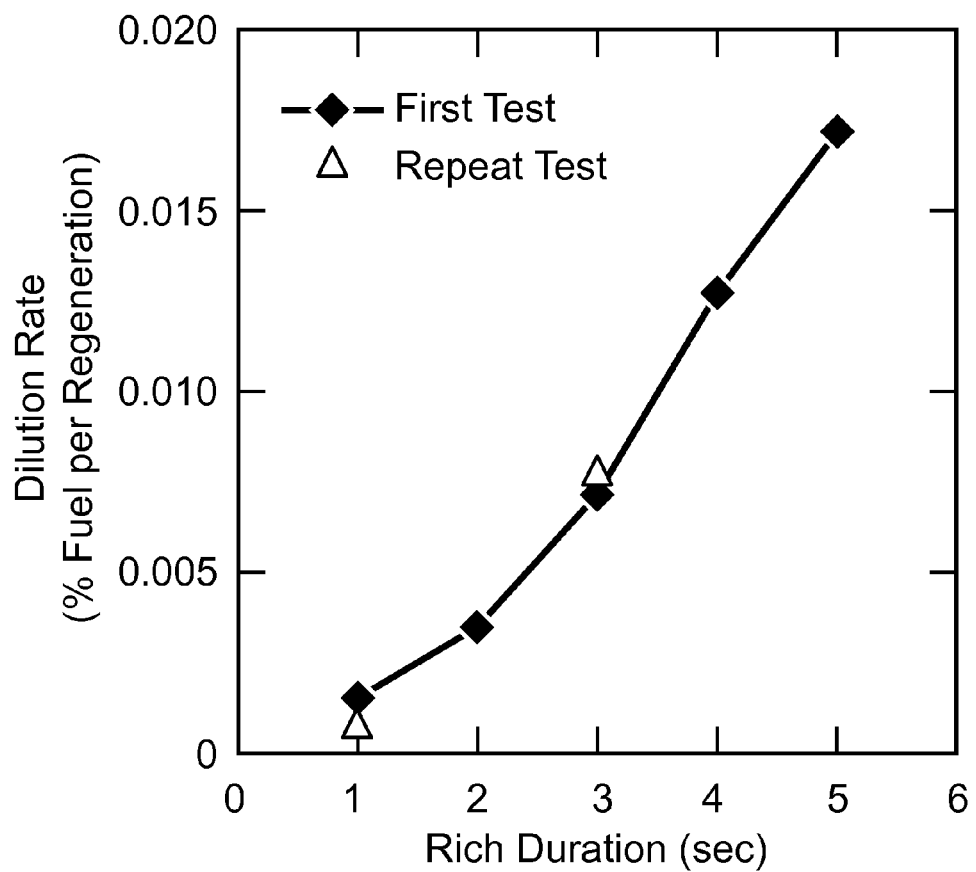
FIG. 15 is a graph showing dilution rate as a function of rich duration for a rich duration experiment.

Rich duration experiments were conducted in which the duration of the rich combustion event was varied from 1 to 5 seconds in 1-second increments. FIG. 14 shows lean events 74, rich events 76, and rich event duration 78. The timing of the fuel addition was 60° past TDC. LIF measurements shown in FIG. 15 indicate an increase in fuel dilution as the rich duration increases; this result corroborates with the other experiments presented hereinabove. The dilution vs. duration plot has some curvature indicating that dilution may increase more as duration increases for constant fueling rate control. Repeat 1-and 3-sec. data points agree well with the sweep data.

Comparison with Standard Method

During the engine-based experiments, oil samples were collected from the engine so that comparisons could be made between the LIF fuel dilution results and measurements of fuel dilution of oil by the standardized methodology for quantifying fuel in oil. The standard method employed was based on an ASTM International standard (D3524-04) for measuring fuel in oil samples, and uses gas chromatography (GC). In the method, diesel fuel and oil are separated in the gas chromatograph. Quantification of the amount of fuel in oil is accomplished by integrating the chromatograph periods for fuel and oil elution and comparing the values to known standards.

Figure 16:
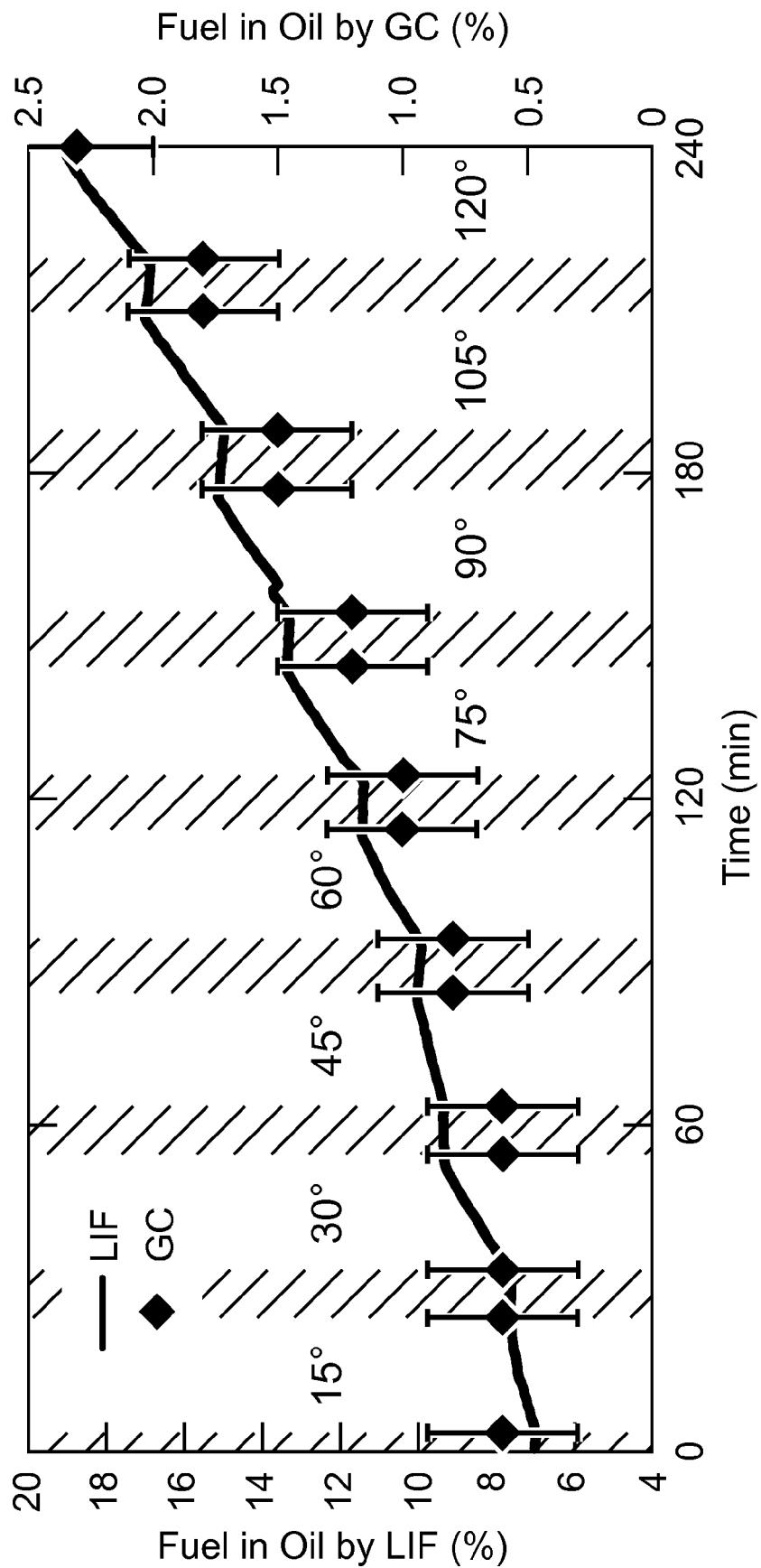
FIG. 16 is a graph showing a comparison of LIF-based and gas chromatograph (GC)-based measurements of oil dilution by fuel.

A comparison of the LIF and GC results is shown in FIG. 16. Data is shown from an experiment to measure the fuel dilution as a function of the timing of extra fuel injection for enrichment. Periods of lean engine operation, shown as hatched regions, occur between periods of lean-rich operation. Each lean-rich operation period represents a different timing for the extra fuel injection which is indicated as crank angle position past top dead center. The experiment is the same type of experiment shown in FIG. 11, but FIG. 16 shows the fuel in oil measurement as a function of time. The slope of the fuel in oil measurement as a function of time combined with the regeneration frequency was used to determine the dilution rate as a function of number of regenerations shown in FIG. 11.

Comparison of the LIF and GC results shown in FIG. 16 highlights similarities and differences between the two methods. Both sets of data clearly show that fuel dilution occurs during the lean-rich periods; fuel in oil levels during the lean-only periods remain essentially constant. Furthermore, both LIF and GC results show that fuel dilution occurs at higher rates for later injection timing; lean-rich cycling with the 120° timing produced the largest changing in fuel dilution for both methods. However, although the LIF and GC data shown the same trends in fuel dilution, the quantity of fuel dilution reported by the two methods is not congruent. For example, the LIF method clearly resolves variations in oil dilution at the 15° and 30° timing, while the GC method does not. Furthermore, over the course of the experiment the LIF method reported a change in fuel in oil from 7 to 19%, but the GC data only showed a change from 0.6 to 2.3%. These ranges differ by a factor of approximately seven.

Several possible reasons for the magnitude differences in the LIF and GC fuel in oil measurements exist. An important difference between the two methods is that the LIF method detects the dye in the fuel, but the GC method detects the fuel components. Since the LIF method measures the dye specifically, any fuel component that would evaporate from the oil is not accounted for in the measurement. The fuel chemistry is complex and different fuel components have different vapor pressures and evaporate from the oil at different rates. In contrast, the dye has a specific chemistry and remains soluble in the oil under normal operating conditions.

For the above reasons, a reasonable explanation of the difference in magnitude for the LIF and GC measurements of fuel in oil is that the LIF method measures the total amount of fuel (or specifically dye) that enters the oil, but the GC method measures the equilibrium level of fuel in the oil attained from both fuel impingement into the oil and fuel evaporation from the oil. Under such an assumption, the factor of seven difference in the measurements indicates that only one-seventh of the fuel that enters the oil system is retained while the majority (six-sevenths) of the fuel evaporates from the oil.

The specific details of the time frames and locations of the fuel evaporation are not known; however, no drop in fuel level in the oil was observed in the bulk oil measurements made during the 10-minute lean periods shown in FIG. 16. Thus, the evaporation could be occurring in the cylinder from the oil film on the cylinder wall. The interactions of the fuel and dye with the cylinder wall oil film in the rapidly changing environment of the combustion chamber are highly complex and dynamic, and further studies with measurements of the dye and fuel pathways to and from the oil film on the cylinder wall would be required to fully characterize the mechanisms. However, a complete understanding of such mechanisms is not considered to be required in order to effectively practice the invention.

Since the dye does not evaporate from the oil like the fuel components, the LIF method more appropriately measures the "dye in oil" as opposed to the "fuel in oil". However, the magnified sensitivity due to the dye enables the LIF method to measure dilution rates in real time with more sensitivity than the GC method. In the data shown in FIG. 16, the LIF method is capable of measuring fuel dilution at the 15° and 30° data points, but the GC does not report any dilution occurring since the GC method is unable to detect small changes in fuel dilution. The error bars in FIG. 16 for the GC data are +/−0.3%, and the lower sensitivity of the GC method makes measurements of low dilution rates more challenging. In contrast, the LIF method is of sufficient precision to detect changes of 0.01% levels of fuel in oil and clearly detects the dilution occurring at the 15° and 30° timing points. Although the precision of the LIF method allows measurement within +/−0.01%, the accuracy of the LIF method was found to be +/−0.1% as changes in the oil LIF spectra over time caused some drift to occur in the quantification. It is contemplated that the greater precision and sensitivity of the LIF method enables real-time feedback on fuel dilution rates which is a utility of the LIF method as a research and development tool.

Changes in the fuel concentration in oil over time can be measured continuously and/or incrementally in time so that the rate of change in fuel in oil can be determined by the method of the present invention. Since measurements and analysis can be performed in real time, the method of the present invention provides useful analysis in applications where rapid feedback on fuel levels in oil is desired.

While there has been shown and described what are at present considered to be examples of the invention, it will be obvious to those skilled in the art that various changes and modifications can be prepared therein without departing from the scope of the inventions defined by the appended claims.

What is claimed is:

1. A method of detecting fuel in oil comprising:
   a. providing an excitation light source for exposing an oil sample to light in order to excite the oil sample from a non-excited state to an excited state, and a spectrally selective device for detecting light emitted from the oil sample as the oil sample returns from the excited state to a non-excited state;
   b. operating said excitation light source to expose the oil sample to excitation light in order to excite the oil sample from a non-excited state to an excited state;
   c. operating said spectrally selective device to detect a fluorescent light signal emitted from the oil sample as the oil sample returns from the excited state to a non-excited state to produce spectral indicia; and
   d. ascertaining the concentration of fuel in the oil sample by comparing a ratio of a fluorescent light signal in two or more spectral regions and/or by comparing a spectral signature of a fluorescent light signal in two or more spectral regions.

2. A method of detecting fuel in oil in accordance with claim 1 wherein said excitation light source comprises at least one light source selected from the group consisting of: a light emitting diode, a laser diode, a non-diode laser, an incandescent device, and a fluorescent device.

3. A method of detecting fuel in oil in accordance with claim 1 wherein the exposing the oil sample to excitation light comprises exciting the oil sample with 532-nm light from a laser diode.

4. A method of detecting fuel in oil in accordance with claim 1 wherein ascertaining the concentration of fuel in the oil sample comprises comparing the ratio of the fluorescent light signal in two or more spectral regions.

5. A method of detecting fuel in oil in accordance with claim 1 wherein ascertaining the concentration of fuel in the oil sample comprises comparing the spectral signature of the fluorescent light signal in two or more spectral regions.

6. A method of detecting fuel in oil in accordance with claim 1 further comprising adding a dye to the fuel prior to the fuel being introduced into the oil sample to augment a fluorescent light signal emitted by the fuel and thereby enhance fuel detection sensitivity.

7. A method of detecting fuel in oil in accordance with claim 1 wherein said excitation light source comprises a diode laser.

8. A method of detecting fuel in oil in accordance with claim 1 further comprising determining a temperature of the oil sample by calibration of fluorescent light signal changes.

9. A method of detecting fuel in oil in accordance with claim 1 further comprising enhancing a signal-to-blank ratio of fuel-in-oil measurement by adding the fuel before fuel is introduced into the oil sample.

10. A method of detecting fuel in oil in accordance with claim 9 wherein the dye is present in the fuel in an amount in the range of 0.05-0.10% by mass.

11. A method of detecting fuel in oil in accordance with claim 9 wherein the dye is a fluorescent dye.

12. A method of detecting fuel in oil in accordance with claim 1 wherein said spectrally selective device comprises a spectrometer.

13. A method of detecting fuel in oil comprising:
   a. providing an oil sample containing oil, fuel and particulates;

b. exposing the oil sample to excitation light from an excitation source thereby exciting the oil sample from a non-excited state to an excited state;

c. detecting a fluorescent light signal emitted from the oil sample; and d. ascertaining the concentration of fuel in the oil sample independent of effect that particulates present in the oil sample have on the fluorescent light signal emitted by the oil sample, by comparing a ratio of the fluorescent light signal in two or more spectral regions and/or by comparing a spectral signature of the fluorescent light signal in two or more spectral regions.

14. The method of claim 13 wherein the excitation source comprises a laser.

15. The method of claim 13 wherein the exposing the oil sample to the excitation source and the exposing the oil sample to the excitation source comprises exciting the oil sample with 532-nm light from a laser.

16. The method of claim 13 further comprising ascertaining the concentration of fuel in the oil sample such that particulates present in the oil sample do not affect the fuel concentration measurement.

17. A method of detecting fuel in oil in accordance with claim 13 further comprising adding a dye to the fuel in an amount in the range of 0.05-0.10% by mass.

18. The method of claim 13 further comprising determining a temperature of the oil sample by calibration of fluorescent light signal changes.

19. The method of claim 13 further comprising enhancing a signal-to-blank ratio of fuel in the oil sample by adding a dye to the fuel prior to the fuel being introduced into the oil sample.

* * * * *

UNITED STATES PATENT AND TRADEMARK OFFICE
CERTIFICATE OF CORRECTION

| | |
|---|---|
| PATENT NO. | : 7,839,492 B2 |
| APPLICATION NO. | : 12/137964 |
| DATED | : November 23, 2010 |
| INVENTOR(S) | : James E. Parks, III and William P. Partridge, Jr. |

It is certified that error appears in the above-identified patent and that said Letters Patent is hereby corrected as shown below:

Column 2, line 9, "includes" should read --including--

Column 8, line 40, "relative" should read --relatively--

Column 11, line 39, "30° 45°" should read --30°, 45°--

Column 14, line 2, claim 1, "inventions" should read --invention--

Column 14, line 54, claim 9, "the fuel" should read --a dye to the fuel--

Columns 15 and 16, lines 16, 17, and 1, claim 15, "wherein the exposing the oil sample to the excitation source and the exposing the oil sample to the excitation source" should read
--wherein the exposing the oil sample to the excitation source--

Signed and Sealed this
Twenty-eighth Day of February, 2012

David J. Kappos
*Director of the United States Patent and Trademark Office*